United States Patent
Stahmann et al.

(10) Patent No.: US 7,616,988 B2
(45) Date of Patent: Nov. 10, 2009

(54) SYSTEM AND METHOD FOR DETECTING AN INVOLUNTARY MUSCLE MOVEMENT DISORDER

(75) Inventors: Jeffrey E. Stahmann, Ramsey, MN (US); Jesse W. Hartley, Lino Lakes, MN (US); Kent Lee, Fridley, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 427 days.

(21) Appl. No.: 10/939,639

(22) Filed: Sep. 13, 2004

(65) Prior Publication Data

US 2005/0080463 A1   Apr. 14, 2005

Related U.S. Application Data

(60) Provisional application No. 60/504,256, filed on Sep. 18, 2003.

(51) Int. Cl.
*A61B 5/04* (2006.01)
*A61B 5/117* (2006.01)
*A61B 5/103* (2006.01)

(52) U.S. Cl. .................... 600/546; 600/595

(58) Field of Classification Search .............. 600/300, 600/301, 392, 483, 523, 534, 546, 554, 587, 600/595, 529, 484, 501, 590; 607/2, 72, 607/48, 17, 42, 45
See application file for complete search history.

(56) References Cited

U.S. PATENT DOCUMENTS

| 4,562,841 | A | 1/1986 | Brockway et al. |
|---|---|---|---|
| 4,958,632 | A | 9/1990 | Duggan |
| 5,036,849 | A | 8/1991 | Hauck et al. |
| 5,047,930 | A | 9/1991 | Martens et al. |
| 5,187,657 | A | 2/1993 | Forbes |
| 5,203,348 | A | 4/1993 | Dahl et al. |
| 5,230,337 | A | 7/1993 | Dahl et al. |
| 5,275,159 | A | 1/1994 | Griebel |
| 5,284,136 | A | 2/1994 | Hauck et al. |

(Continued)

FOREIGN PATENT DOCUMENTS

WO    99/04841    4/1999

(Continued)

OTHER PUBLICATIONS

Olusola et al., *Nightcap: Laboratory and home-based evaluation of a portable sleep monitor*, 32 Psychophysiology, 32-98 (1995). Abstract only.

(Continued)

*Primary Examiner*—Max Hindenburg
*Assistant Examiner*—Brian Szmal
(74) *Attorney, Agent, or Firm*—Hollingsworth & Funk, LLC

(57) ABSTRACT

Methods and systems are directed to evaluating a pathological condition and involve acquiring muscle movement signals, such as electromyogram (EMG) or accelerometer signals, and detecting the presence of the pathological condition. Methods and systems also provide for detecting sleep-related involuntary muscle disorders and non sleep-related involuntary muscle disorders using muscle movement signals. Drug therapy, transcutaneous electric nerve stimulation therapy, or other therapy may be delivered to treat a detected or diagnosed involuntary muscle disorder.

27 Claims, 11 Drawing Sheets

U.S. PATENT DOCUMENTS

| | | | |
|---|---|---|---|
| 5,313,953 A | 5/1994 | Yomtov et al. | |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,483,969 A | 1/1996 | Testerman et al. | |
| 5,540,727 A | 7/1996 | Tockman et al. | |
| 5,545,202 A | 8/1996 | Dahl et al. | |
| 5,603,732 A | 2/1997 | Dahl et al. | |
| 5,697,951 A | 12/1997 | Harpstead et al. | |
| 5,716,377 A * | 2/1998 | Rise et al. | 607/2 |
| 5,836,987 A | 11/1998 | Baumann et al. | |
| 5,916,243 A | 6/1999 | KenKnight et al. | |
| 5,974,340 A | 10/1999 | Kadhiresan | |
| 6,044,298 A | 3/2000 | Salo et al. | |
| 6,055,454 A | 4/2000 | Heemels | |
| 6,076,015 A | 6/2000 | Hartley et al. | |
| 6,181,961 B1 | 1/2001 | Prass | |
| 6,221,011 B1 | 4/2001 | Bardy | |
| 6,270,457 B1 | 8/2001 | Bardy | |
| 6,277,072 B1 | 8/2001 | Bardy | |
| 6,280,380 B1 | 8/2001 | Bardy | |
| 6,306,088 B1 * | 10/2001 | Krausman et al. | 600/301 |
| 6,310,085 B1 | 10/2001 | Willis | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,398,728 B1 | 6/2002 | Bardy | |
| 6,440,066 B1 | 8/2002 | Bardy | |
| 6,544,199 B1 * | 4/2003 | Morris | 600/590 |
| 6,881,192 B1 * | 4/2005 | Park | 600/529 |
| 7,039,468 B2 * | 5/2006 | Freed et al. | 607/72 |
| 2001/0031930 A1 | 10/2001 | Roizen et al. | |
| 2002/0169485 A1 * | 11/2002 | Pless et al. | 607/48 |
| 2002/0193697 A1 | 12/2002 | Cho et al. | |
| 2003/0023184 A1 | 1/2003 | Pitts-Crick et al. | |
| 2003/0055461 A1 | 3/2003 | Girouard et al. | |
| 2003/0100925 A1 | 5/2003 | Pape et al. | |
| 2003/0149457 A1 * | 8/2003 | Tcheng et al. | 607/48 |
| 2003/0153954 A1 | 8/2003 | Park et al. | |
| 2003/0163059 A1 | 8/2003 | Poezevera et al. | |
| 2003/0178031 A1 | 9/2003 | Du Pen et al. | |
| 2003/0199945 A1 | 10/2003 | Ciulla | |
| 2004/0088027 A1 | 5/2004 | Burnes et al. | |
| 2004/0111040 A1 * | 6/2004 | Ni et al. | 600/534 |
| 2004/0138719 A1 | 7/2004 | Cho et al. | |
| 2005/0165323 A1 | 7/2005 | Montgomery et al. | |

FOREIGN PATENT DOCUMENTS

| | | |
|---|---|---|
| WO | 02/087696 | 11/2002 |

OTHER PUBLICATIONS

Verrier et al., *Sleep, dreams, and sudden death: the case for sleep as an autonomic stress test for the heart*, Cardiovascular Research 31 (1996), pp. 181-211.

Verrier et al., *Sleep Related Cardiovascular Risk: New Home—Based Monitoring Technology for Improved Diagnosis and Therapy*, A.N.E., Apr. 1997, vol. 2, No. 2, pp. 158-175.

* cited by examiner

SYSTEM AND METHOD FOR DETECTING AN INVOLUNTARY MUSCLE MOVEMENT DISORDER

RELATED PATENT DOCUMENTS

This application claims the benefit of Provisional Patent Application Ser. No. 60/504,256, filed on Sep. 18, 2003, to which priority is claimed pursuant to 35 U.S.C. §119(e) and which is hereby incorporated herein by reference.

FIELD OF THE INVENTION

The invention relates generally to implantable medical devices and methods, and, more particularly, to devices and methods for detecting an involuntary muscle movement disorder.

BACKGROUND OF THE INVENTION

Restless Leg Syndrome (RLS) and Periodic Limb Movement Disorder (PLMD) are closely associated disorders also known as Myoclonus and Ekbom Syndrome, respectively. RLS and PLMD affect 2-8% of the population in the United States. Both conditions are characterized by involuntary movements of the limbs, most typically the legs.

RLS occurs during periods of wakefulness. PLMD occurs during sleep or in transitions from wakefulness to sleep or sleep to wakefulness. Patients with RLS or PLMD may suffer twitching, tingling, aching, burning, itching, or pulling sensations in their arms and/or legs. Patients with RLS often suffer from PLMD, but people with PLMD do not always have RLS. Because RLS patients may also suffer from sleep-related PLMD, these patients are often awakened, and their ability to return to sleep is delayed by RLS.

RLS patients are unable to sit still and may have to remain active to relieve limb discomfort. For patients suffering from RLS, relaxation and passive activities become increasingly problematic, adversely affecting quality of life.

For both PLMD and RLS patients, sleep quality deteriorates. When a patient tries to fall asleep, the leg discomfort begins. In severe cases, patients only sleep a few hours at night, resulting in excessive daytime sleepiness and disruption of the normal daily routine. RLS and PLMD patients often complain of irritability, anxiety, and depression. The severity of RLS and/or PLMD ranges from infrequent minor discomfort to daily agony that leads some patients to contemplate suicide.

Symptoms of PLMD may come and go through the night and over the course of one's life. PLMD episodes may last a few minutes or several hours. There may be an interval of days, weeks or months between episodes. PLMD patients may experience sudden but rhythmic limb jerks occurring periodically, e.g., every 20 to 40 seconds. PLMD episodes may be seen primarily in the first third of the night, during non-REM sleep. Patients with RLS often have PLMD, but patients with PLMD do not always have RLS. Polysomnographic studies indicate that about 70% to 90% of patients with RLS have PLMD.

PLMD movements may be characterized, for example, by periodic flexion of one or both legs involving bending at the hip and knee with upward bending of the foot and the great toe, resembling a flexion reflex. A normal healthy person may have five of these movements per hour. The diagnosis of PLMD is given when more than five movements per hour occur.

Both genders are affected, with a slightly higher incidence in women. These conditions are seen more commonly with advancing age. The prevalence of PLMD or RLS is 2% of the population of ages less than 30, 5% of ages 30 to 50, and 25% of ages 50-60. The highest prevalence is seen in age 65 or older, with 44% of the population affected. While usually diagnosed in older groups, these disorders may be traced to childhood. Hyperactive, fidgeting children or youths often labeled with "growing pains" may actually be showing the early manifestations of PLMD and RLS.

SUMMARY OF THE INVENTION

The present invention is directed to systems and methods for evaluating pathological conditions associated with an involuntary limb movement disorder. According to one embodiment, a method of evaluating a pathological condition involves sensing muscle movement signals, and implantably detecting presence of an involuntary muscle movement disorder using the muscle movement signals. Sensing the muscle movement signals may be preformed implantably and externally. Detecting presence of the involuntary muscle movement disorder may involve detecting a sleep-related involuntary muscle movement disorder and/or a non sleep-related involuntary muscle movement disorder using the sensed muscle movement signals.

Detecting presence of the involuntary muscle movement disorder may involve detecting a disease or pathological syndrome using the muscle movement signals. Detecting presence of the involuntary muscle movement disorder may involve detecting conditions associated with bruxism, periodic limb movement disorder, restless leg syndrome, muscular dystrophy, muscle inflammation, pinched nerves, peripheral nerve damage, amyotrophic lateral sclerosis, myasthenia gravis, and disc herniation, for example.

Sensing muscle movement signals may involve acquiring data from a sensor directly detecting physical movement, such as an accelerometer. Sensing muscle movement signals may involve acquiring data from a sensor detecting bio-electrical changes associated with movement, such as an electromyogram sensor. Sensing muscle movement signals may involve acquiring data from sensors detecting physical movement and bio-electrical changes.

Onset and offset of sleep may be detected, for purposes of discriminating between sleep-related and non sleep-related involuntary limb movement conditions, for example. Sensed muscle movement signals and/or information associated with the detected involuntary muscle movement disorder may be communicated to a patient-external processing system, such as a network, or to a patient-internal processing system.

A therapy based on one or both of the muscle movement signals and the detected involuntary muscle movement disorder may be delivered to the patient. For example, a drug therapy, nerve stimulation therapy, or other therapy may be delivered to treat the detected involuntary muscle movement disorder.

According to another embodiment, a system for evaluating a pathological condition includes a sensor configured to sense movement of skeletal musculature, a detector coupled to the sensor, and an implantable processor coupled to the detector. The processor is configured to determine presence of an involuntary muscle movement disorder, such as those discussed above.

In one configuration, one of the sensor and detector includes an implantable component. In another configuration, each of the sensor and detector includes an implantable component. The sensor may include one or both of electromyogram (EMG) sensors and an accelerometer. A sleep detector may be coupled to the processor, and the processor may detect a sleep-related involuntary muscle movement disorder and/or a non sleep-related involuntary muscle movement disorder.

The system may include a communication interface coupled to the processor. The communication interface may be configured to effect connectivity between the processor and a patient-external processing system, such as an external network. The system may also include a therapy delivery system configured to deliver a therapy to treat the involuntary muscle movement disorder, such as a drug therapy device, nerve stimulation therapy, or other therapy device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
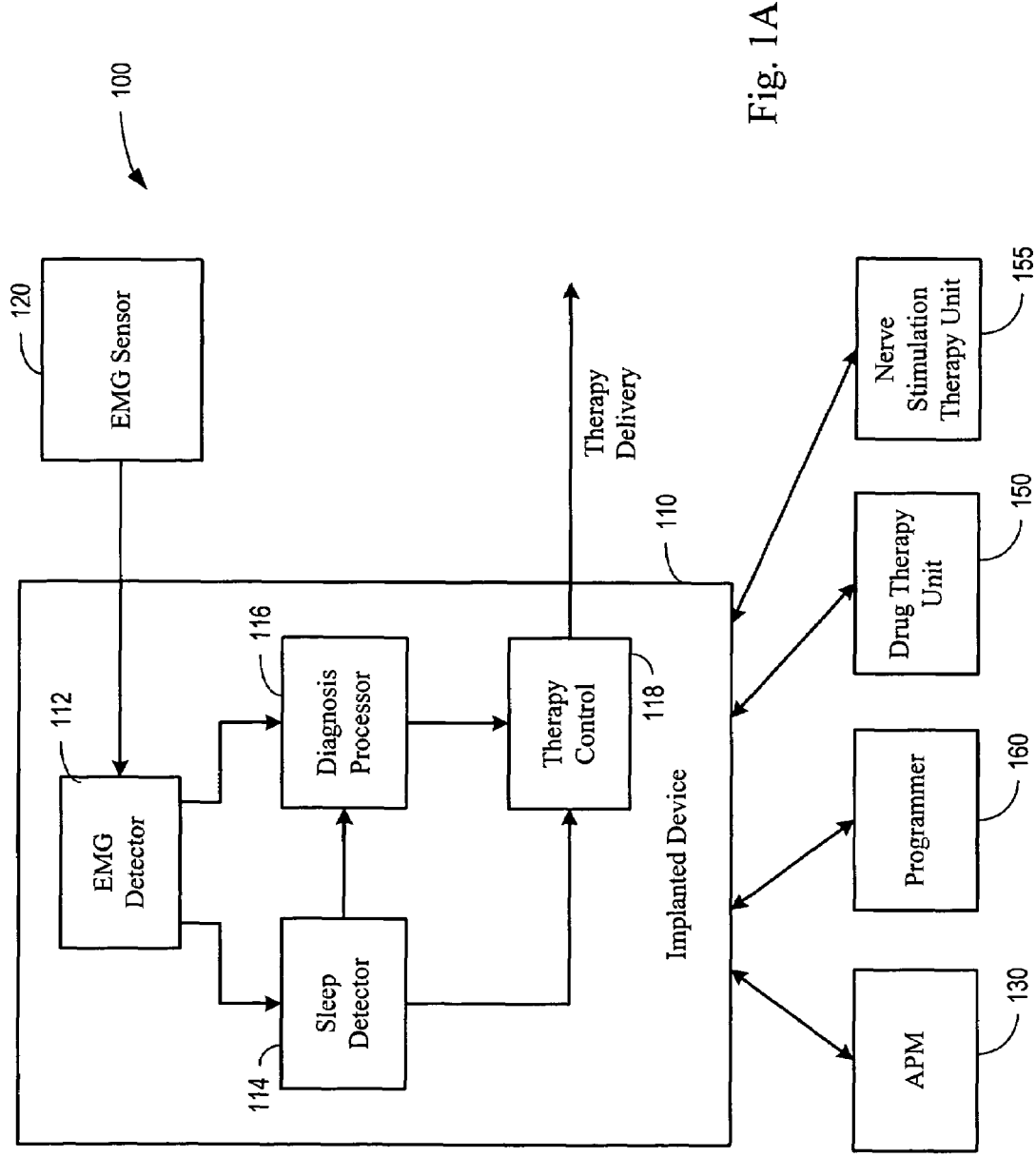
FIGS. 1A-1C are block diagrams of systems implementing diagnosis of medical conditions using muscle movement information in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the invention.

Methods, devices and systems in accordance with the present invention may include one or more of the features, structures, methods, or combinations thereof described herein. It is intended that methods, devices and systems in accordance with the present invention need not include all of the features and functions described herein, but may be implemented to include selected features and functions that provide for useful structures and/or functionality.

Disorders and diseases affecting the interdependent physiological systems of the human body may be more effectively diagnosed and treated using a coordinated approach. Various embodiments of the invention are implemented using medical systems employing one or a number of patient-internal and/or patient-external medical devices. Medical devices may communicate or otherwise operate in concert or in a stand-alone manner to provide more comprehensive patient monitoring, diagnosis, and therapy.

The present invention is directed to systems and methods that acquire and process muscle movement signals in an implantable or partially implantable device. Information acquired from muscle movement sensors may be used in connection with patient monitoring, diagnosis, and therapy. An implantable system may incorporate muscle movement detection for various purposes, including disease diagnosis, sleep detection, and therapy control, among other functions. Systems may include one or more movement sensors, which may be implemented as one or more patient-internal and/or one or more patient external movement sensors. For example, systems may include one or more electromyogram (EMG) sensors, which may be implemented as one or more patient-internal and/or one or more patient external EMG sensors. Systems may alternatively, or additionally, include one or more accelerometers to detect muscle movement, and may further be used to detect patient sleep and non sleep.

An EMG sensor detects the electrical activity of muscles during muscle activity. When muscles are active, they produce an electrical current that is proportional to the level of the muscle activity. Electromyogram sensing devices of the present invention may facilitate diagnosis of many pathological conditions. These conditions include, for example, muscular dystrophy, inflammation of muscles, pinched nerves, peripheral nerve damage (damage to nerves in the arms and legs), amyotrophic lateral sclerosis (ALS, also known as Lou Gehrig disease), myasthenia gravis, disc herniation, and movement disorders such as periodic limb movement, restless limb movement, and bruxism.

Embodiments of the present invention are directed to systems and methods for screening and/or diagnosing an involuntary limb movement condition, such as Restless Leg Syndrome (RLS) or Periodic Limb Movement Disorder (PLMD). In accordance with embodiments of the invention, PLMD, RLS, and/or other movement disorders such as bruxism, for example, may be diagnosed using a system that is fully or partially implantable. A partially or fully implantable system, such as a cardiac rhythm management system, may incorporate a movement detector. One or more movement sensors are coupled to the movement detector within the implantable device. The movement sensors may include any sensor or any combination of sensors capable of detecting motion and/or muscle activity associated with motion, such as accelerometers, electromyogram (EMG) sensors, and/or a combination of one or more accelerometers and one or more EMG sensors.

Signals from the movement sensors may be received and processed by the movement detector in the implantable device. The movement data may be stored in the implantable device or communicated to an external processing system, either of which may process the sensed movement information. Movement information may be processed, trended, displayed, etc. locally or remotely to detect presence of an involuntary limb movement condition.

Embodiments of the present invention are directed to implementing components and/or functions of an electromyogram sensor in an implanted or partially implanted medical device. Information acquired from the electromyogram sensor(s) may be used in connection with patient monitoring, diagnosis, and therapy.

The following discussion, with reference to FIG. 1A, describes embodiments of the invention involving disease diagnosis using an EMG in an implanted device. The processes and systems exemplified by these embodiments may be implemented alone or in combination with one or more processes and systems exemplified by other embodiments described or incorporated herein to provide a coordinated approach to patient monitoring, diagnosis, and/or therapy.

FIG. 1A illustrates an implantable system 100 incorporating EMG detection that may be used for disease diagnosis, sleep detection, and therapy control, among other functions. In accordance with various embodiments, the system 100 includes one or more EMG sensors 120, which may be implemented as one or more patient-internal and/or one or more patient external EMG sensors.

The EMG sensor or sensors 120 may be positioned in or on the patient's body at one or more selected locations to sense electrical muscular activity at the one or more selected locations. The location of the EMG sensor or sensors 120 depends on the specific application. For example, one or more EMG sensors 120 may be positioned intramuscularly or on the surface of the skin above the muscle to detect the electrical activity of the muscle.

Intramuscular placement of EMG sensors involves inserting a needle electrode through the skin into the muscle whose electrical activity is to be measured. Because skeletal muscles are often large, several needle electrodes may need to be placed at various locations to obtain an accurate reading of muscle activity.

Signals from EMG sensor or sensors 120 may be transmitted to an EMG detector 112 of the implanted device 110 through leads or using a wireless communications link. The EMG detector 112 receives signals from the EMG sensor or sensors 120 and processes the signals for use by a diagnosis processor 116 and/or a sleep detector 114, for example. A number of muscle-related disorders occur primarily while the patient is asleep. Information about the patient's sleep stage may be used to enhance sleep monitoring and/or diagnosis of a variety of disorders. In addition, it may be useful to provide a first therapy while the patient is awake and a second therapy while the patient is asleep. Detection of EMG signals may be used to diagnose disorders as well as trigger sleep-time therapy. Collected data may be stored, displayed, printed, or transmitted to a separate device.

By way of example, the sleep detector 114 may use EMG information to determine various sleep stages, including REM sleep. In one implementation, one or more EMG sensors 120 may be placed on the patient's face to facilitate the detection of REM sleep. For example, one or more surface EMG sensors 120 may be placed on the patient's chin or jaw, e.g., on the mentalis muscle and/or submentalis muscle, to detect muscle atonia associated with rapid eye movement sleep.

In another implementation, one or more EMG sensors 120 may be placed on the housing, header, or lead of an implanted device 110 positioned in the pectoral region of the patient. In this configuration, the EMG sensors 120 may be used to detect atonia of the pectoral muscles during REM sleep. A sleep detector 114 may use information from the EMG detector 112 to facilitate the detection of sleep onset and offset, and to determine the various stages of sleep. Detection of sleep stages may be used, for example, in patient monitoring, diagnosis and/or therapy for various disorders. Techniques involving EMG sensors 120 positioned on an implantable device 110, such as a CRM device, are described in commonly owned U.S. patent application Ser. No. 10/643,006 filed Aug. 18, 2003 and entitled "Sleep State Classification," which is incorporated by reference herein in its entirety.

The diagnosis processor 116 may use EMG-related information to diagnose a variety of diseases or disorders such as those listed above. Disease/disorder diagnosis may be facilitated using information acquired from the EMG detector 112 associated with the patient's muscle activity, limb movements, and respiratory motions, for example. The diagnosis processor 116 may also use information about the patient's sleep stages to aid in diagnosis. In various embodiments, the diagnosis processor 116 may use EMG information to diagnose muscle and/or nerve disorders, such as those caused by muscle inflammation and/or muscular dystrophy for example. The EMG information may be used to diagnose muscle weakness due to nerve disorders, including pinched nerves, peripheral nerve damage, amyotrophic lateral sclerosis (ALS), myasthenia gravis, and disc herniation, for example. The EMG information may be used to diagnose a variety of movement disorders, such as periodic limb movement disorders and/or restless legs syndrome.

In yet another embodiment, diagnosis of various movement disorders, such as PLMD, RLS, and bruxism (nighttime teeth grinding) may be facilitated using one or more EMG sensors 120 coupled to an implantable device 110. Periodic limb movement disorder and restless leg syndrome are disorders that involve undesirable movements of the limbs as described in more detail below.

One or more EMG sensors 120 may be placed in or on the muscles of the limbs or other muscles to detect limb movements. For example, EMG sensors 120 placed on or in the anterior tibialis muscles may be used to identify leg movements associated with PLMD and/or RLS. EMG sensors 120 placed on the jaw may be used to identify tempomanidibular disorders such as nighttime teeth grinding or other involuntary jaw movements.

EMG-related information may be trended, stored, displayed, or transmitted from the implantable device 110 to another device. In one embodiment, information from the EMG detector 112, the sleep detector 114, and/or the diagnosis processor 116 is downloaded to a remote device, such as a programmer 160 or an advanced patient management (APM) device 130 for further analysis by the APM device 130, programmer 160 and/or the patient's physician.

Information from the EMG detector, 112 the sleep detector 114, and/or the diagnosis processor 116 may optionally be used to adjust therapy provided to a patient. Therapy provided by the implanted device 110 may be adjusted by the patient's physician or by a remote device, such as the APM device 130 or programmer 160. In one example, the patient's physician may send a command through the programmer 160 or APM device 130 to a therapy control unit 118 in the implanted device 110 to initiate, terminate, or modify therapy. In another example, the APM device 130 and/or the programmer 160 may automatically command the implanted device 110 to adjust therapy based on analysis performed in the APM device 130 and/or the programmer 160. In another embodiment, the therapy control unit 118 of the implanted device 110 may use information from the EMG detector 112, the sleep detector 114, and/or the diagnosis processor 116, to automatically adjust therapy provided to a patient.

The EMG-related information acquired by the implantable device 110 may be transferred to other therapy devices (internal or external), such as drug delivery devices 150 and/or nerve stimulation therapy devices 155. For example, transcutaneous electric nerve stimulation may improve symptoms in some RLS sufferers who also have PLMD. Electrical stimulation may be applied to an area of the legs or feet, usually before bedtime, for about 15 to 30 minutes. Transcutaneous electric nerve stimulation therapy has been found to be helpful in reducing nighttime leg jerking.

The transferred information may be used to adjust the therapy delivered by the drug therapy device 150, nerve stimulation therapy device 155, and/or other therapy device, or used in further diagnosis and/or monitoring functions, for example. Examples of drugs useful with the drug therapy device 150 include dopamine agents (muscle relaxers), benzodiazepines (sedatives), anti-convulsants (to reduce muscle activity), and opioids (narcotics to reduce motor activity).

Although the sleep detector 114, the diagnosis processor 116, and the therapy control unit 118 are illustrated internal to the implantable device 110, it is contemplated that any or all of these components may be patient-external in alternate embodiments, and may be incorporated into other components such as the APM 130, for example. Similarly, the drug delivery devices 150 and/or nerve stimulation devices 155, illustrated patient-external in FIG. 1A, may be included in the implantable device 110 in alternate embodiments.

Figure 1B:
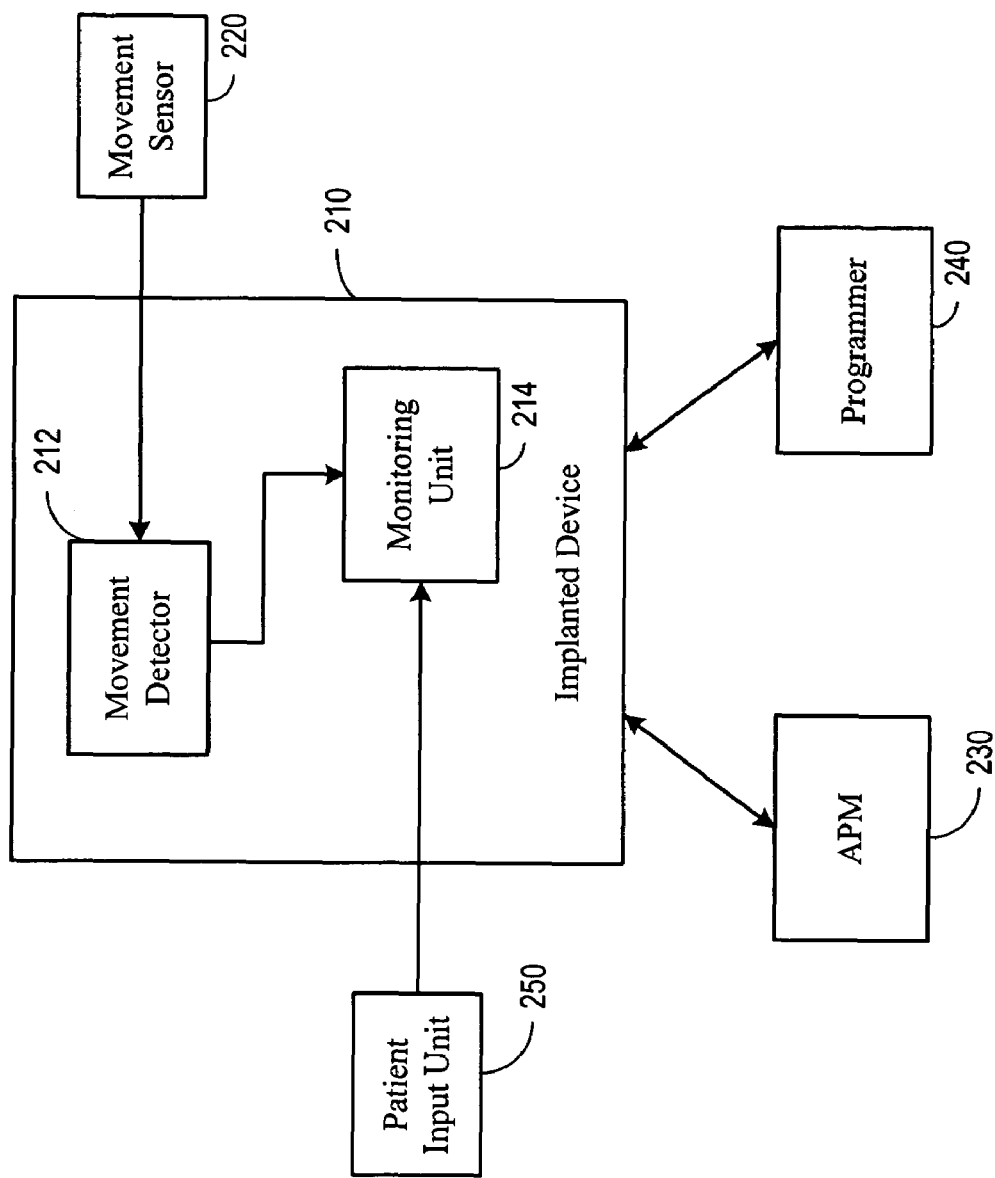
Figure 1C:
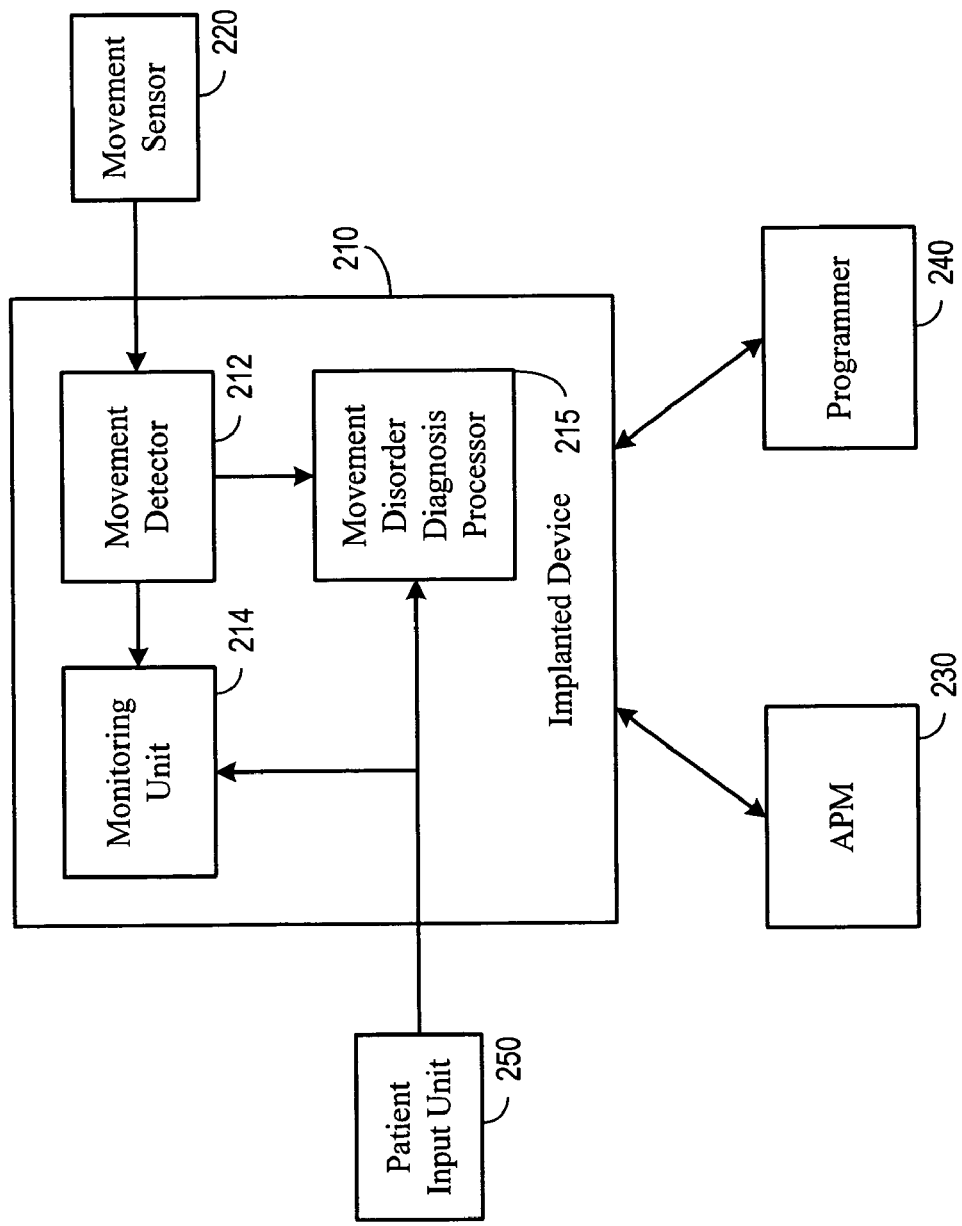
Figure 1E:
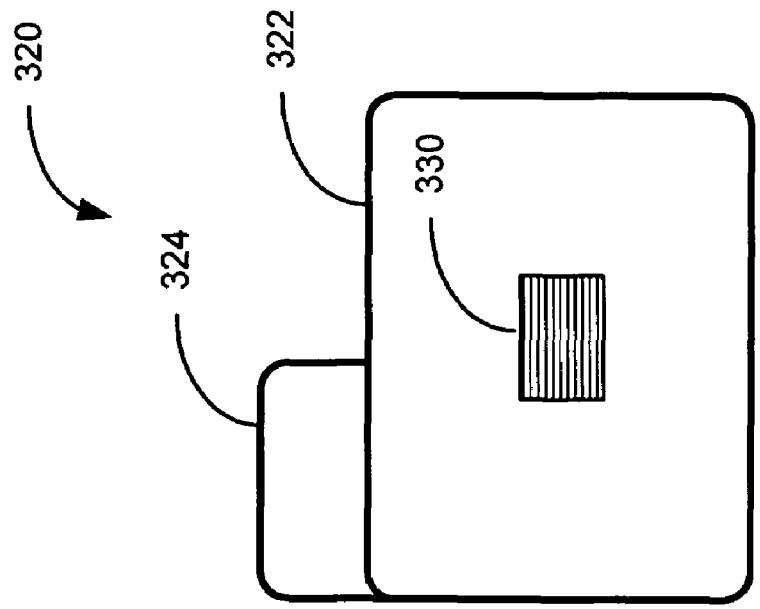
FIGS. 1D-1G are diagrams illustrating various configurations of sensors coupled to an implanted medical device in accordance with embodiments of the invention.
Figure 1D:
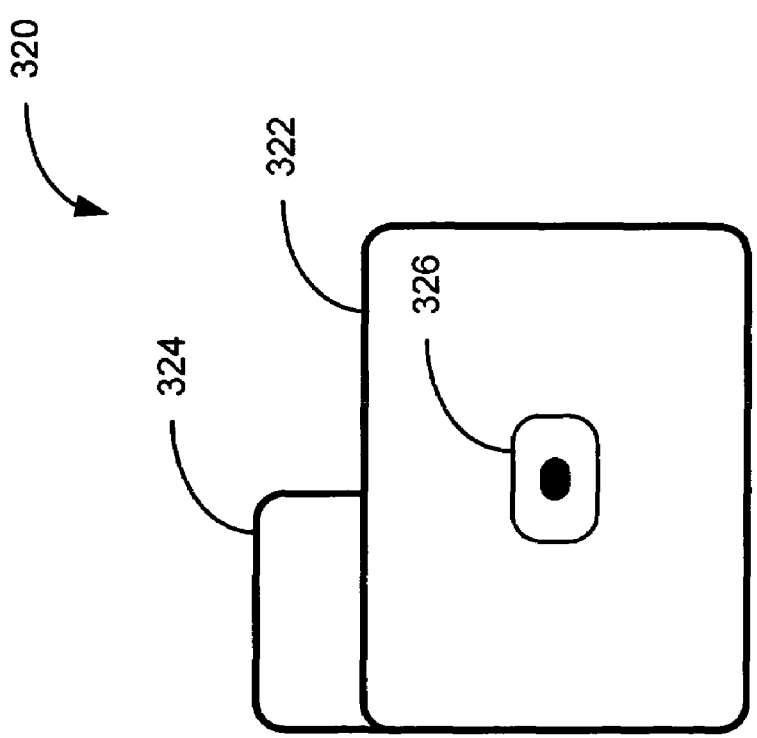

The following discussion, with reference to FIGS. 1B-1C, describes embodiments of the invention involving detection of movement disorders. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, PLMD, RLS, and/or other movement disorders such as bruxism, for example, may be diagnosed using a system that is fully or partially implantable. FIG. 1B illustrates an implantable medical device, e.g., a CRM that incorporates a movement detector 212. One or more movement sensors 220 are coupled to the movement detector 212 within an implantable device 210.

The movement sensors 220 may include any sensor or any combination of sensors capable of detecting motion and/or muscle activity associated with motion. For example, the patient's movements may be detected using one or more accelerometers, one or more EMG sensors, and/or a combination of one or more accelerometers and one or more EMG sensors.

In one embodiment, one or more movement sensors (e.g., accelerometers and/or EMG sensors) are coupled to the patient at appropriate locations to detect movements of the extremities, e.g., limb movements, or other movements. Signals from the movement sensors 220 are received and processed by a movement detector 212 in the implantable device 210. The movement detector 212 may cooperate with a memory in a monitoring unit 214 to store information about the detected movements. Movement information may be stored, trended, displayed, and/or transmitted to a separate device, such as an APM system 230 or a programmer 240 for further operations.

In another embodiment, illustrated in FIG. 1C, one or more movement sensors 220 are coupled to a movement detector 212 within the implantable device 210, as previously discussed. The implantable device 210 also includes a movement disorder diagnosis processor 215 that receives movement information from the movement detector 212. The movement disorder diagnosis processor 215 evaluates the movement information to determine if the movements are consistent with various movement disorders such as RLS and/or PLMD.

In one example, the movement sensors 220 may include one of more EMG sensors placed on or in the anterior tibialis. Typical EMG bursts due to PLMD movements may last between 0.5-5 seconds and may recur every 20-40 seconds, for example. The movement disorder diagnosis processor 215 may make a diagnosis of PLMD if at least about 40 EMG bursts are detected within an 8-hour sleep period, for example.

Sleep disruption caused by the PLMD movements may be determined by any or a combination of the sleep detection techniques described herein, including, for example, brain wave (EEG) sensing and/or a combination of respiration (e.g., minute ventilation) and activity sensing, among others. Alternately or additionally, detection of sleep disruption, such as by using a minute ventilation sensor, may be used to confirm PLMD. Movement disorder diagnosis may be downloaded to a programmer 240, an APM system 230, or other therapeutic or diagnostic device.

In accordance with another embodiment of the invention, RLS diagnosis may involve patient input regarding their symptoms. For example, as illustrated in FIGS. 1B and 1C, a patient input device 250 may be used to acquire information from the patient regarding the patient's perception of symptoms. The patient may be prompted to rate their symptoms on a scale of 0 to 4, or some other scale, for example with a lower number representing fewer RLS symptoms and higher number representing greater RLS symptoms, for example. The patient input may be acquired using the patient input device 250 over a period of days, for example, about three days to about nine days to establish a diagnosis. Patient input through the patient input device 250 may also be acquired after diagnosis and/or treatment, for example to assess status of the disorder or the efficacy of treatment.

For example, if the patient input is acquired over a period of six days, the maximum score is 24, i.e., a score of four for each or six days. In this scenario, a score greater than about 12 suggests a diagnosis of severe RLS. A score of about six to about twelve suggests a diagnosis of moderate RLS.

In the embodiment illustrated in FIG. 1B, information about RLS symptoms may be acquired by the patient input device 250 and transmitted to an APM device 230, the programmer 240, or other device for monitoring, display, storage, evaluation, and/or diagnosis. In the embodiment illustrated in FIG. 1C, the information acquired by the patient input device 250, along with the movement information, may be used by the movement disorder diagnosis processor 215 in the implantable device 210 to make a diagnosis of RLS.

Embodiments of the present invention are directed to methods and systems for diagnosis of movement disorders such as PLMD and RLS. RLS diagnosis may be complicated due to the symptom based nature of the RLS diagnosis. The use of patient input through a patient-input device provides a system for collection of symptom based information. Because PLMD and RLS are related disorders, the diagnosis of PLMD through movement detection techniques described herein may be used to enhance the RLS diagnosis.

Use of the methods and systems of the invention may reduce the need for in-clinic sleep studies typically used for movement disorder diagnosis. Further, daily measurements may be made over a number of days which is not practical for in-clinic studies. Earlier and more frequent diagnosis of movement disorders may be enabled using the systems and methods of the invention.

FIGS. 1D-1G illustrate various configurations of an EMG sensor mechanically coupled to an implanted medical device 320, such as an implantable pacemaker or implantable cardioverter/defibrillator in accordance with embodiments of the invention, which may be useful for diagnosing diseases such as sleep-related muscle disorders. The implantable medical device 320 may include a housing 322 enclosing the medical device circuitry and a header 324 for coupling a lead system 340 to the circuitry of the medical device 320.

Figure 1G:
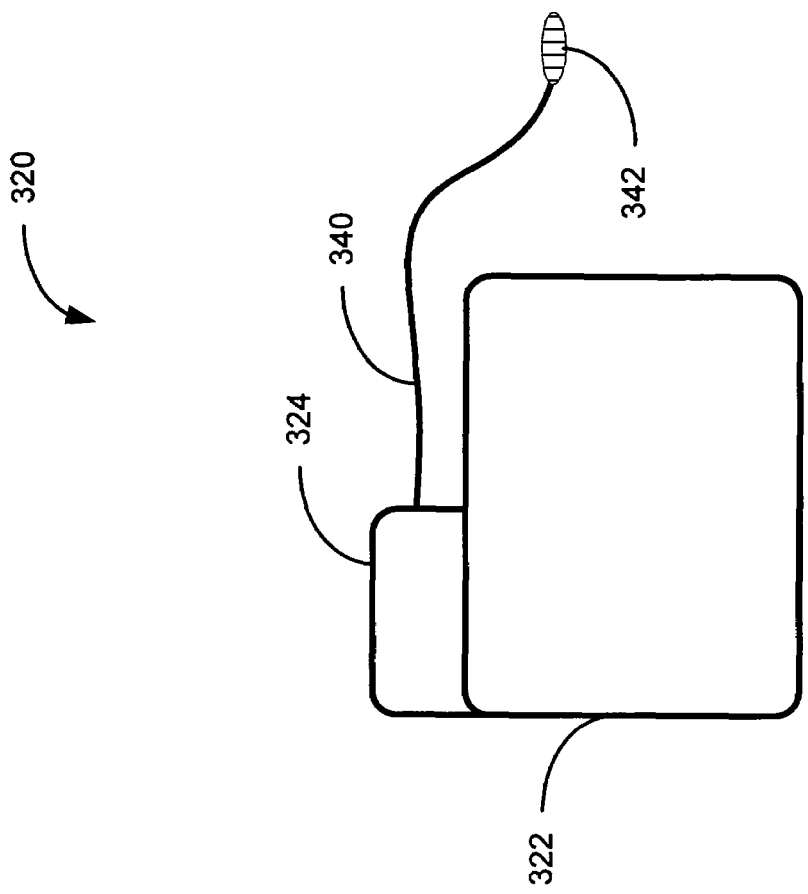
Figure 1F:
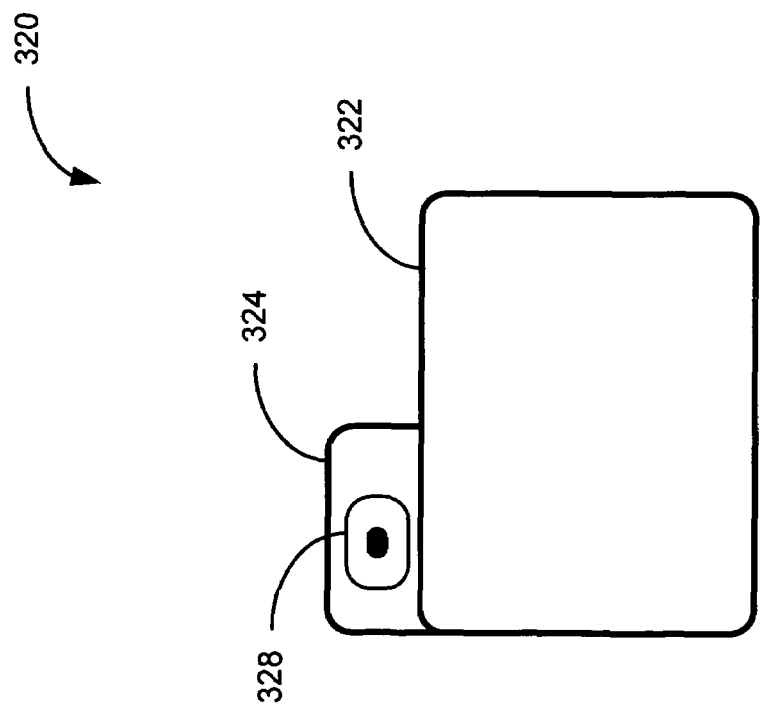

A movement sensor may be implemented, for example, to include an EMG sensor that employs one or more EMG electrodes 326 or a force responsive sensor 330 positioned on the housing 322 of the medical device 320 as illustrated in FIGS. 1F and 1G, respectively. FIG. 1F illustrates one or more EMG electrodes 328 positioned on the header 324 of the medical device 320. Alternatively, a movement sensor 342 (e.g., one that includes one or more EMG electrodes or a strain gauge) may be positioned on the lead system 340 or may be coupled to the housing 322 through a catheter or lead system 340, such as by using the header 324, as illustrated in FIG. 1G.

Figure 2:
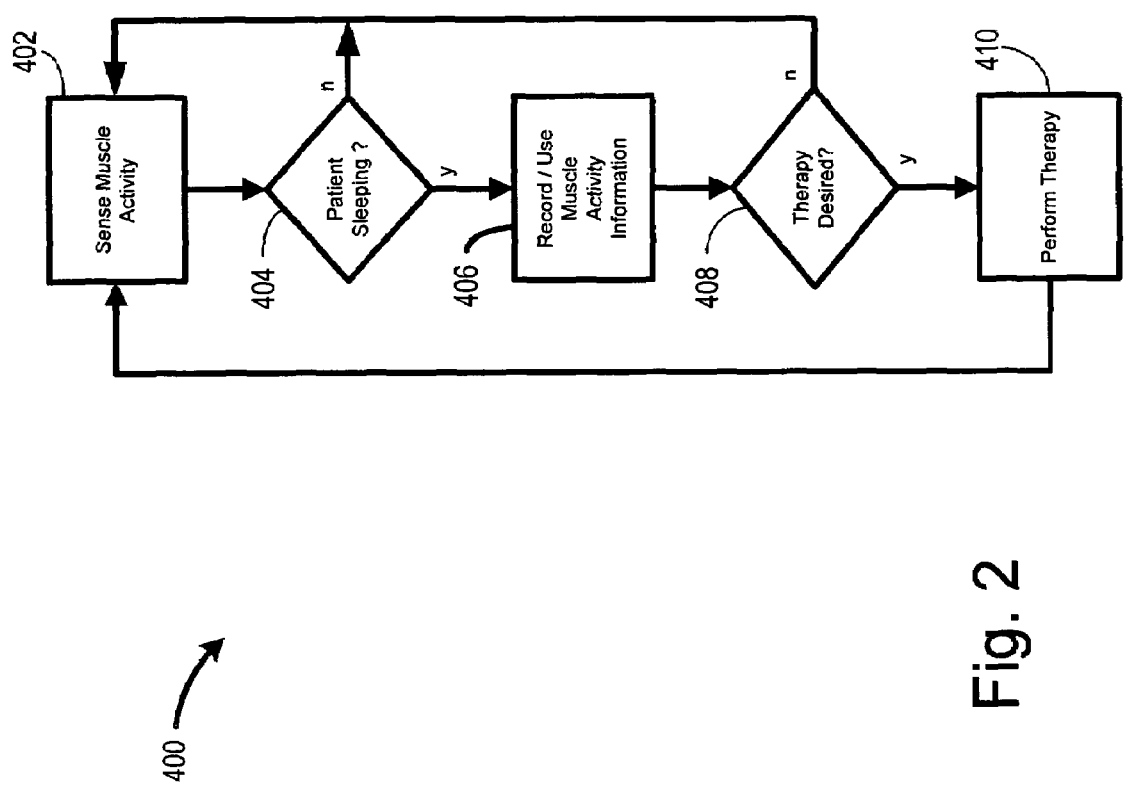
FIG. 2 is a flow chart illustrating an EMG based algorithm in accordance with embodiments of the invention.

FIG. 2 illustrates a method 400 of implantably sensing and detecting movement used for diagnosis of sleep-related muscle disorders. A muscle activity signal is sensed at a block 402. Muscle activity may be sensed, for example, using EMG sensors, accelerometers, or other sensors suitable for determining patient movement. A determination block 404 is used to decide if the patient is sleeping. If determination 404 decides the patient is not sleeping, the method 400 loops back to the beginning.

If the patient is determined to be sleeping at block 404, the muscle activity sensed at block 402 provides information recorded at block 406. For example, date, time, sensor data, sense signal amplitudes or other information may be useful for updating, developing, and/or determining a muscle disorder index, a diagnosis, a sleep-related muscle activity history, and other parameters useful for patient diagnosis and treatment. The information recorded at block 406 may be useful, for example, to predict, verify, classify, and/or determine the existence of a sleep-related muscle disorder.

If intervention and/or treatment is desired at determination block 408, the intervention and/or treatment may be performed at block 410 before re-starting the method 400. For example, the intervention at block 410 may be the automatic activation of a medical process, modification of a patient's CRM stimulation, modification of a therapy, notification to a patient-external device and/or a physician, or other desirable action.

Figure 3:
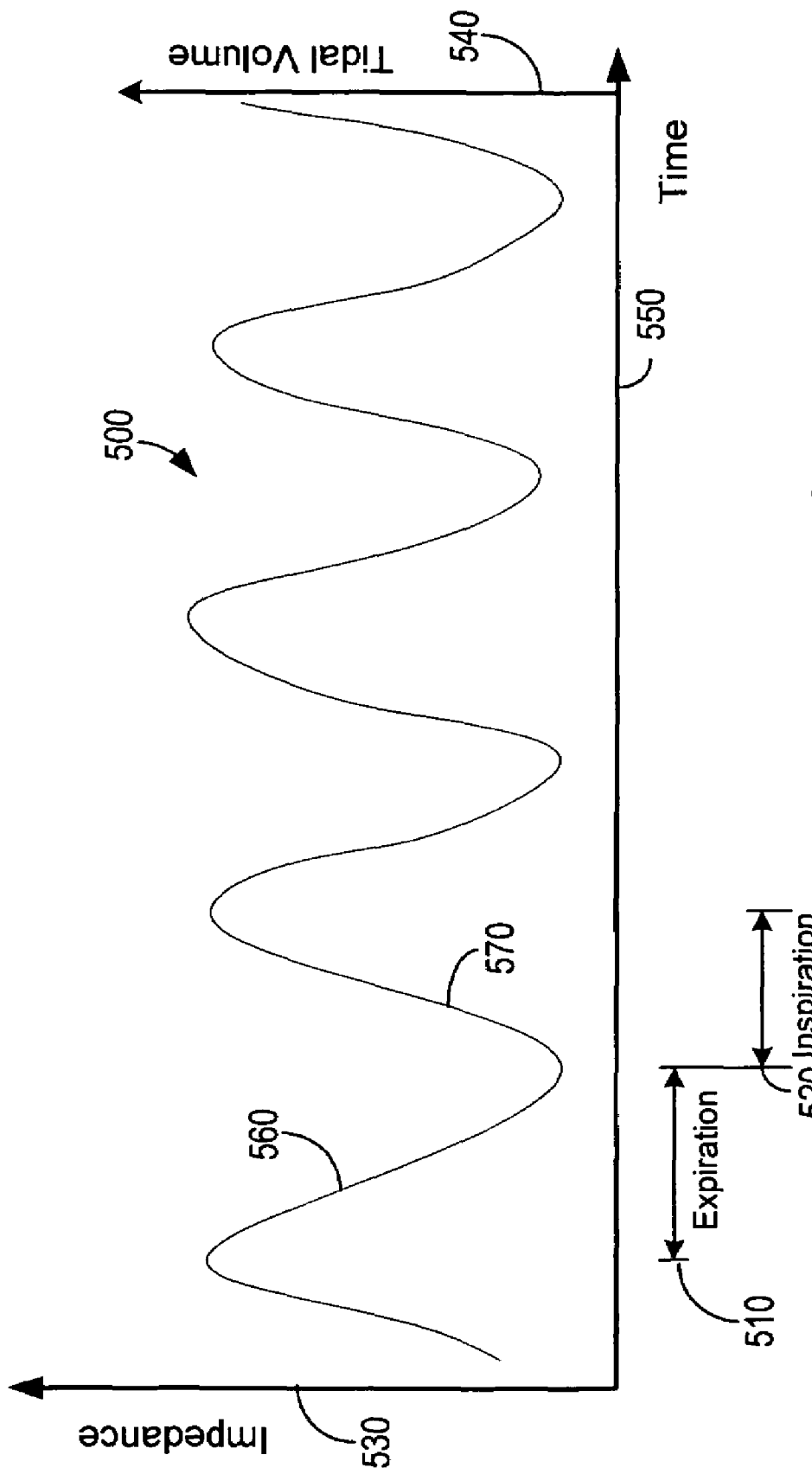
FIG. 3 is a graph of a normal respiration signal measured by a transthoracic impedance sensor that may be utilized for coordinated monitoring, diagnosis and/or therapy in accordance with embodiments of the invention.

Referring now to FIG. 3, an impedance signal 500 is illustrated. The impedance signal 500 may be developed, for example, from an impedance sense electrode in combination with a CRM device. The impedance signal 500 is proportional to the transthoracic impedance, illustrated as an impedance 530 on the abscissa of the left side of the graph in FIG. 3.

The impedance 530 increases 570 during any respiratory inspiration 520 and decreases 560 during any respiratory expiration 510. The impedance signal 500 is also proportional to the amount of air inhaled, denoted by a tidal volume 540, illustrated on the abscissa of the right side of the graph in FIG. 3. The variations in impedance during respiration, identifiable as the peak-to-peak variation of the impedance signal 500, may be used to determine the respiration tidal volume 540. Tidal volume 540 corresponds to the volume of air moved in a breath, one cycle of expiration 510 and inspiration 520. A minute ventilation may also be determined, corresponding to the amount of air moved per a minute of time 550 illustrated on the ordinate of the graph in FIG. 3.

Figure 4:
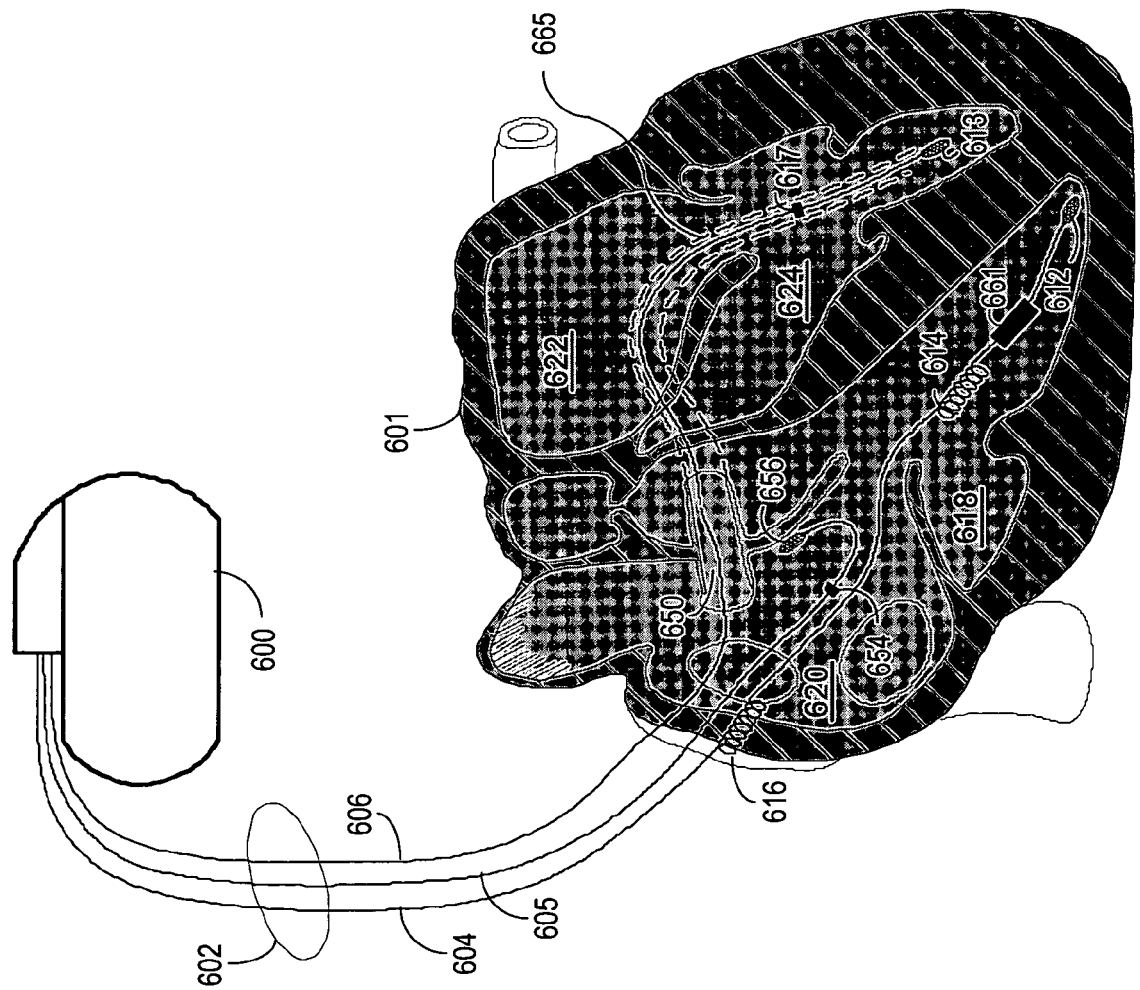
FIG. 4 is an illustration of an implantable cardiac device including a lead assembly shown implanted in a sectional view of a heart, the device used for coordinated patient monitoring, diagnosis, and/or therapy in accordance with embodiments of the invention.

Referring now to FIG. 4, the implantable device illustrated in FIG. 4 is an embodiment of a CRM device that includes an implantable pacemaker/defibrillator 600 electrically and physically coupled to an intracardiac lead system 602. The CRM device shown in FIG. 4 may be used and/or modified to cooperate with other sensors or devices for coordinated patient monitoring, diagnosis, and/or therapy in accordance with embodiments of the invention. The intracardiac lead system 602 is implanted in a human body with portions of the intracardiac lead system 602 inserted into a heart 601. Electrodes of the intracardiac lead system 602 may be used to detect and analyze cardiac signals produced by the heart 601 and to provide stimulation and/or therapy energy to the heart 601 under predetermined conditions, to treat cardiac arrhythmias of the heart 601.

The CRM 600 depicted in FIG. 4 is a multi-chamber device, capable of sensing signals from one or more of the right and left atria 620, 622 and the right and left ventricles 618, 624 of the heart 601 and providing pacing pulses to one or more of the right and left atria 620, 622 and the right and left ventricles 618, 624. Low energy pacing pulses may be delivered to the heart 601 to regulate the heart beat or maintain a cardiac rhythm, for example. In a configuration that includes cardioversion/defibrillation capabilities, high energy pulses may also be delivered to the heart 601 if an arrhythmia is detected that requires cardioversion or defibrillation.

The intracardiac lead system 602 includes a right ventricular lead system 604, a right atrial lead system 605, and a left ventricular lead system 606. The right ventricular lead system 604 includes an RV-tip pace/sense electrode 612, an RV-coil electrode 614, and an RV-ring electrode 661.

One or more electrodes of the lead system 602 may be used as transthoracic impedance sensors to facilitate acquisition of the patient's respiration waveform, or other respiration-related information. The transthoracic impedance electrodes may include, for example, one or more intracardiac electrodes 616, 614, 654, 656, 612, 617, 613, 661 positioned in one or more chambers of the heart 601. The intracardiac electrodes 616, 614, 654, 656, 612, 617, 613, 661 may be coupled to impedance drive/sense circuitry positioned within the housing of the pulse generator.

In one implementation, impedance drive/sense circuitry generates a current that flows through the tissue between an impedance drive electrode 654 and a can electrode on the housing of the pulse generator. The voltage at an impedance sense electrode 656 relative to the can electrode changes as the patient's transthoracic impedance changes. The voltage signal developed between the impedance sense electrode 656 and the can electrode is detected by the impedance sense circuitry. Other locations and/or combinations of impedance sense and drive electrodes are also possible.

The voltage signal developed at the impedance sense electrode 656, illustrated in FIG. 3, is proportional to the patient's transthoracic impedance and represents the patient's respiration waveform. The transthoracic impedance increases during respiratory inspiration 520 and decreases during respiratory expiration 510. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration—expiration cycles without substantial interruptions, as indicated in FIG. 3.

The RV-tip electrode 612 is positioned at an appropriate location within the right ventricle 618 for pacing the right ventricle 618 and sensing cardiac activity in the right ventricle 618. The right ventricular lead system may also include one or more defibrillation electrodes 614, 616, positioned, for example, in the right ventricle 618 and the superior vena cava, respectively.

The atrial lead system 605 includes A-tip and A-ring cardiac pace/sense electrodes 656, 654. In the configuration of FIG. 4, the intracardiac lead system 602 is positioned within the heart 601, with a portion of the atrial lead system 605 extending into the right atrium 620. The A-tip and A-ring electrodes 656, 654 are positioned at an appropriate location within the right atrium 620 for pacing the right atrium 620 and sensing cardiac activity in the right atrium 620.

The lead system 602 illustrated in FIG. 4 also includes a left ventricular lead system 606. The left ventricular lead system 606 may include, one or more electrodes 617, 613 positioned within a coronary vein 665 of the heart 601. Additionally, or alternatively, one or more electrodes may be positioned in a middle cardiac vein, a left posterior vein, a left marginal vein, a great cardiac vein or an anterior vein.

The left ventricular lead system 606 may include one or more endocardial pace/sense leads that are advanced through the superior vena cava (SVC), the right atrium 620, the valve of the coronary sinus, and the coronary sinus 650 to locate the LV-distal 613 and LV-proximal 617 electrodes at appropriate locations adjacent to the left atrium 622 and left ventricle 624, respectively. In one example, lead placement involves creating an opening in a percutaneous access vessel, such as the left subcdavian or left cephalic vein. For example, the lead system 602 may be guided into the right atrium 620 of the heart via the superior vena cava.

From the right atrium 620, the left ventricular lead system 606 is deployed into the coronary sinus ostium, the opening of the coronary sinus 650. The left ventricular lead system 606 is guided through the coronary sinus 650 to a coronary vein of the left ventricle 624. This vein is used as an access pathway for leads to reach the surfaces of the left atrium 622 and the left ventricle 624 which are not directly accessible from the right side of the heart. Lead placement for the left ventricular lead system 606 may be achieved via subclavian vein access. For example, a preformed guiding catheter may be used for insertion of the left ventricular electrodes 613, 617 adjacent the left ventricle 624.

Additional configurations of sensing, pacing and defibrillation electrodes may be included in the intracardiac lead system 602 to allow for various sensing, pacing, and defibrillation capabilities of multiple heart chambers. In other configurations, the intracardiac lead system 602 may have only a single lead with electrodes positioned in the right atrium or the right ventricle to implement single chamber cardiac pacing. In yet other embodiments, the intracardiac lead system 602 may not include the left ventricular lead 606 and may support pacing and sensing of the right atrium and right ventricle only. In other embodiments, one or more electrodes positioned on the surface of the heart 601 may be used for pacing the left atrium and/or other cardiac chambers. Any lead and electrode arrangements and configurations are considered to be within the scope of the present system in accordance with embodiments of the invention.

Figure 5:
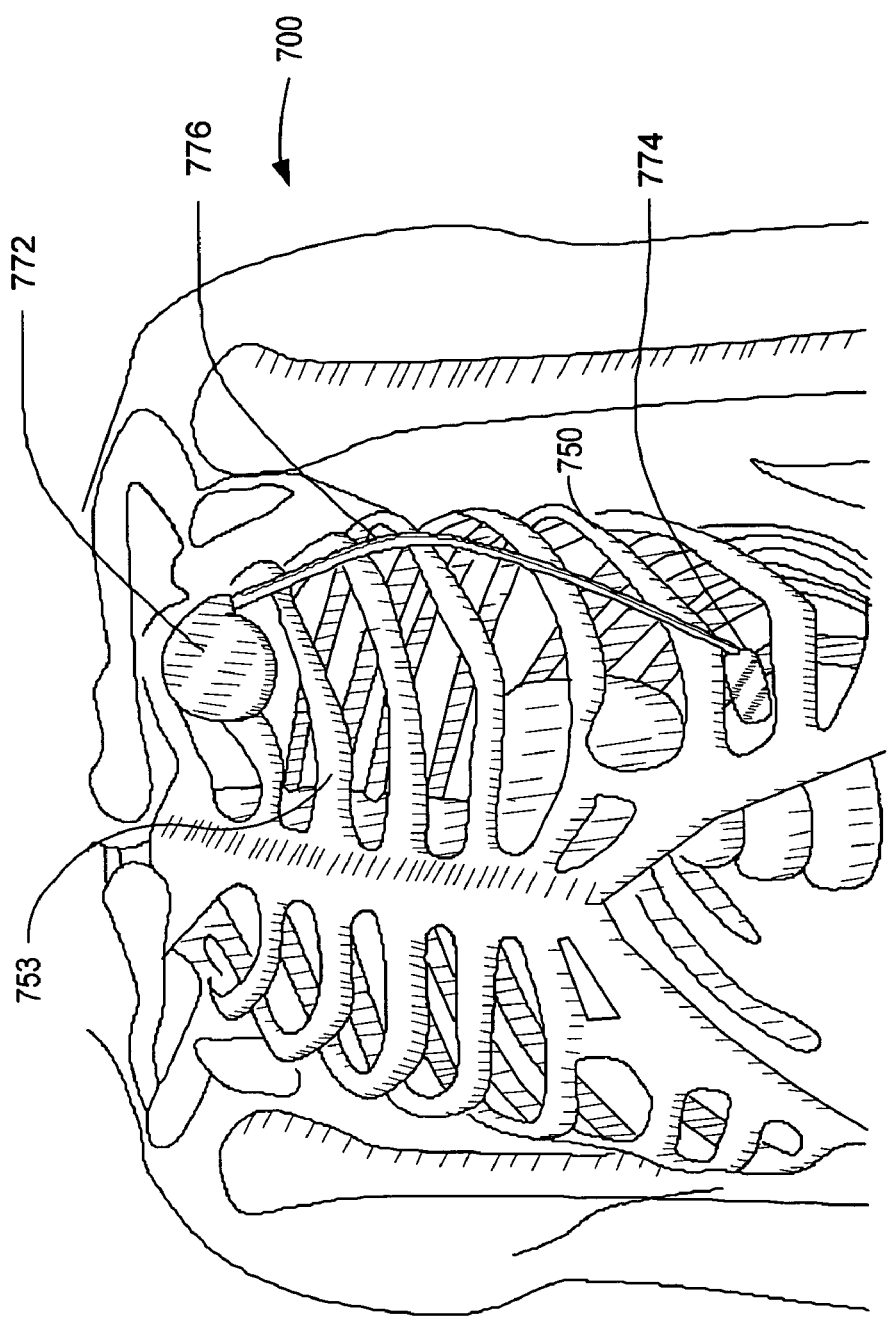
FIG. 5 is an illustration of a thorax having an implanted subcutaneous medical device that may be used for coordinated patient monitoring, diagnosis, and/or therapy in accordance with an embodiment of the invention.

FIG. 5 is a diagram illustrating a subcutaneous implantable medical device 700 that may be used for detecting EMGs and determining the presence of sleep-related muscle disorders in accordance with embodiments of the invention. The device 700 illustrated in FIG. 5 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 750 at an intercostal or subcostal location, within the abdomen, or in the upper chest region (e.g., subclavian location, such as above a third rib 753). In one implementation, one or more electrodes may be located on a primary housing 772 and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

In particular configurations, systems and methods may perform functions traditionally performed by pacemakers, such as providing various pacing therapies as are known in the art, in addition to cardioversion/defibrillation therapies. Exemplary pacemaker circuitry, structures and functionality, aspects of which may be incorporated in an ITCS device of a type that may benefit from multi-parameter sensing configurations, are disclosed in commonly owned U.S. Pat. Nos. 4,562,841; 5,284,136; 5,376,476; 5,036,849; 5,540,727; 5,836,987; 6,044,298; and 6,055,454, which are hereby incorporated herein by reference in their respective entireties. It is understood that ITCS device configurations may provide for non-physiologic pacing support in addition to, or to the exclusion of, bradycardia and/or anti-tachycardia pacing therapies.

An ITCS device in accordance with various embodiments may implement diagnostic and/or monitoring functions as well as provide cardiac stimulation therapy. Diagnostics functions may involve storing, trending, displaying, transmitting, and/or evaluating various indications based on the detection of EMG. Exemplary monitoring circuitry, structures and functionality, aspects of which may be incorporated in an ITCS of the invention, are disclosed in commonly owned U.S. Pat. Nos. 5,313,953; 5,388,578; and 5,411,031, which are hereby incorporated herein by reference in their respective entireties.

An ITCS device may be used to implement various diagnostic functions, which may involve performing rate-based, pattern and rate-based, and/or morphological tachyarrhythmia discrimination analyses. Subcutaneous, cutaneous, and/or external sensors, such as those previously described, may be employed to acquire physiologic and non-physiologic information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

In FIG. 5, there is shown a configuration of an ITCS device having components implanted in the chest region of a patient at different locations. In the particular configuration shown in FIG. 5, the ITCS device includes the housing 772 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 772 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 772 is typically configured to include one or more electrodes (e.g., can electrode and/or indifferent electrode). Although the housing 772 is typically configured as an active can, it is appreciated that a non-active can configuration may be implemented, in which case at least two electrodes spaced apart from the housing 772 are employed.

In the configuration shown in FIG. 5, a subcutaneous electrode 774 may be positioned under the skin in the chest region and situated distal from the housing 772. The subcutaneous and, if applicable, housing electrode(s) may be positioned about the heart at various locations and orientations, such as at various anterior and/or posterior locations relative to the heart. The subcutaneous electrode 774 is coupled to circuitry within the housing 772 via a lead assembly 776. One or more conductors (e.g., coils or cables) are provided within the lead assembly 776 and electrically couple the subcutaneous electrode 774 with circuitry in the housing 772. One or more sense, sense/pace or defibrillation electrodes may be situated on the elongated structure of the electrode support, the housing 772, and/or the distal electrode assembly (shown as subcutaneous electrode 774 in the configuration shown in FIG. 5).

The elongated structure may be formed from a structural plastic, composite or metallic material, and may include, or may be covered by, a biocompatible material. Appropriate electrical isolation between the housing 772 and subcutaneous electrode 774 is provided in cases where the elongated structure is formed from an electrically conductive material, such as metal.

In one configuration, the electrode support assembly and the housing 772 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 772. The electrode support assembly includes mechanical and electrical couplings that facilitate mating engagement with corresponding mechanical and electrical couplings of the housing 772. For example, a header block arrangement may be configured to include both electrical and mechanical couplings that provide for mechanical and electrical connections between the electrode support assembly and housing 772. The header block arrangement may be provided on the housing 772 or the electrode support assembly. Alternatively, a mechanical/electrical coupler may be used to establish mechanical and electrical connections between the electrode support assembly and housing 772. In such a configuration, a variety of different electrode support assemblies of varying shapes, sizes, and electrode configurations may be made available for physically and electrically connecting to a standard ITCS device housing 772.

Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned US Patent Applications: "Subcutaneous Cardiac Sensing, Stimulation, Lead Delivery, and Electrode Fixation Systems and Methods," Ser. No. 60/462,272, filed Apr. 11, 2003; "Reconfigurable Subcutaneous Cardiac Device," Ser. No. 10/821,248, filed Apr. 8, 2004; and "Subcutaneous Cardiac Rhythm Management," Ser. No. 10/820,642, filed Apr. 8, 2004; each hereby incorporated herein by reference.

Figure 6:
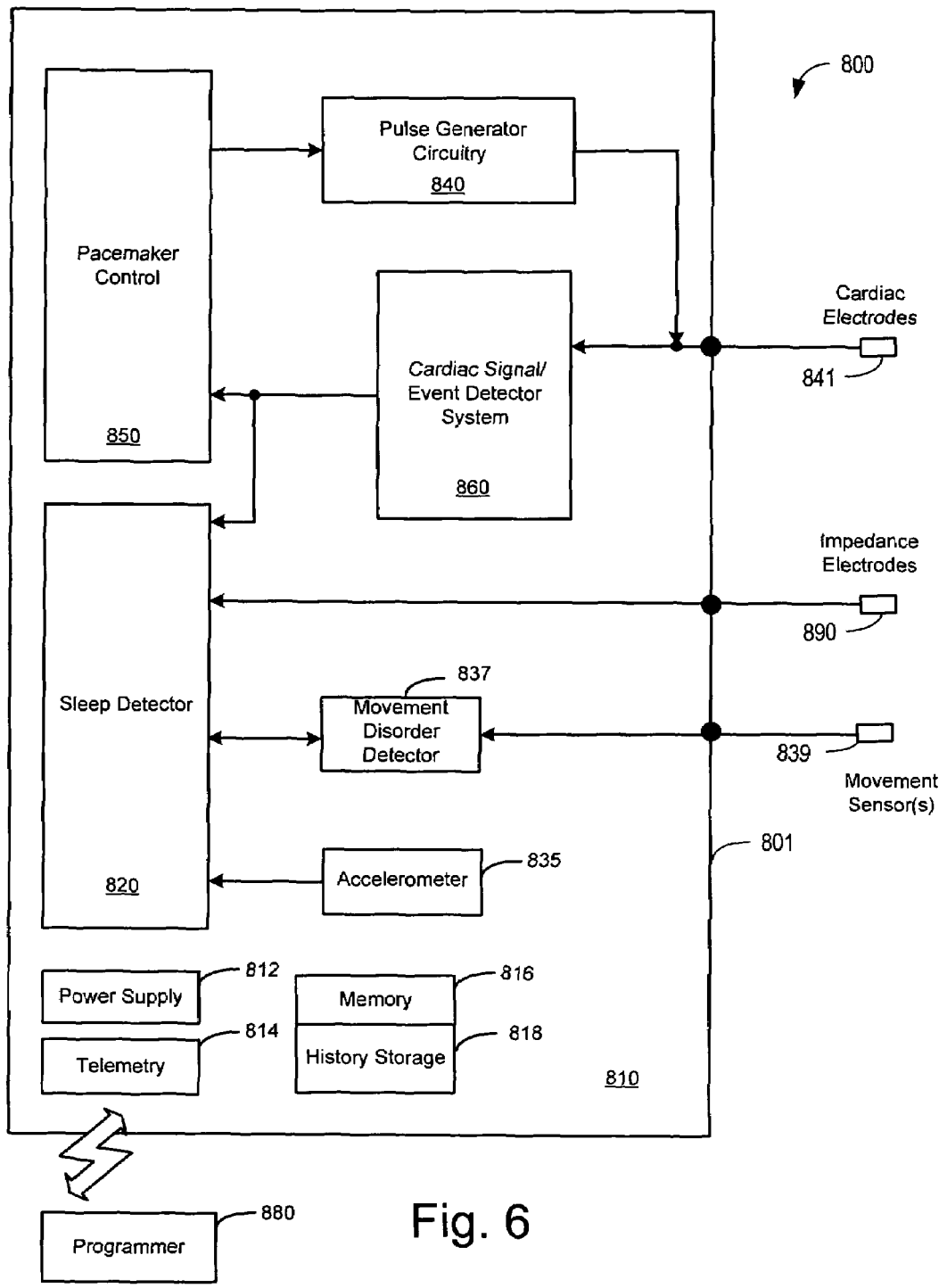
FIG. 6 is a block diagram of a cardiac rhythm management (CRM) system configured as a pacemaker and suitable for implementing a sleep detection methodology in accordance with embodiments of the invention.

Referring now to FIG. 6, there is shown a block diagram of an embodiment of a CRM system 800 configured as a pacemaker and suitable for implantably detecting EMGs and determining the presence of sleep-related muscle disorders in accordance with the invention. FIG. 6 shows the CRM 800 divided into functional blocks. The CRM 800 includes a sleep detector 820 for receiving sleep-related signals and detecting sleep in accordance with embodiments of the invention.

In one embodiment, the sleep detector 820 is incorporated as part of CRM circuitry 810 encased and hermetically sealed in a housing 801 suitable for implanting in a human body. Power to the CRM 800 is supplied by an electrochemical battery power supply 812 housed within the CRM 800. A connector block (not shown) is additionally attached to the CRM 800 to allow for the physical and electrical attachment of the cardiac lead system conductors to the CRM circuitry 810.

The CRM circuitry 810 may be configured as a programmable microprocessor-based system, with circuitry for detecting sleep in addition to providing pacing therapy to the heart. Cardiac signals sensed by one or more cardiac electrodes 841 may be processed by the cardiac event detection circuitry 860. Pace pulses controlled by the pacemaker control 850 and generated by the pulse generator 840 are delivered to the heart to treat various arrhythmias of the heart.

The memory circuit 816 may store parameters for various device operations involved in sleep detection and/or cardiac pacing and sensing. The memory circuit 816 may also store data indicative of sleep-related signals received by components of the CRM circuitry 810, such as information derived from one or more impedance electrodes 890, the cardiac signal detector system 860, the accelerometer 835, and/or the sleep detector 820.

As illustrated in FIG. 6, the sleep detector 820 receives signals derived from the cardiac event detector 860, the impedance electrodes 890 and the accelerometer 835 to perform operations involving detecting sleep onset and sleep termination according to the principles of the invention. Historical data storage 818 may be coupled to the sleep detection circuitry 820 for storing historical sleep related data. Such data may be transmitted to an external programmer unit 880 and used for various diagnostic purposes and as needed or desired.

Also shown in FIG. 6 is a movement disorder detector 837 coupled to one or more movement sensors 839. The movement disorder detector 837 receives signals from the movement sensor(s) 839 from which one or more movement disorders are detected, such as bruxism, periodic limb movement disorder, or restless leg syndrome. The movement sensor(s) 839 are preferably of a type described previously. The movement disorder detector 837 may also be coupled to the sleep detector 820. The sleep detector 820 may determine patient sleep status, such as sleep onset, offset, and arousal, using signals received from the movement sensor(s) 839 and/or from the movement disorder detector 837. The movement disorder detector 837 may use sleep status/state information received from the sleep detector 820 to discriminate between sleep and wakeful movement disorders.

Telemetry circuitry 814 is coupled to the CRM circuitry 810 to allow the CRM 800 to communicate with a remote device such as the programmer 880, or other device. In one embodiment, the telemetry circuitry 814 and the programmer 880 use a wire loop antenna and a radio frequency telemetric link to receive and transmit signals and data between the programmer 880 and telemetry circuitry 814. In this manner, programming commands and data may be transferred between the CRM circuitry 810 and the one or more remote devices 880 during and after implant.

The programming commands allow a physician to set or modify various parameters used by the CRM system 800. These parameters may include setting sleep detection parameters for use during sleep detection, such as which sleep-related signals are to be used for sleep detection and threshold adjustment, and the initial sleep detection thresholds. In addition, the CRM system 800 may download to the programmer 880 stored data pertaining to sensed sleep periods, including the amount of time spent sleeping, the time of day sleep periods occurred, historical data of sleep times, and the number of arousals during the sleep periods, for example.

Still referring to FIG. 6, signals associated with patient activity may be detected through the use of an accelerometer 835 positioned within the housing 801 of the CRM 800. The accelerometer 835 may be responsive to patient activity. The accelerometer signal may be correlated with activity level or workload, for example. Signals derived from the accelerometer 835 are coupled to the sleep detector 820 and may also be used by the pacemaker 850 for implementing a rate adaptive pacing regimen, for example.

The impedance electrodes 890 sense the patient's transthoracic impedance. The transthoracic impedance may be used to calculate various parameters associated with respiration. Impedance driver circuitry (not shown) induces a current that flows through the blood between the impedance drive electrode and a can electrode on the housing 801 of the CRM 800. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 820 for further processing.

Figure 7:
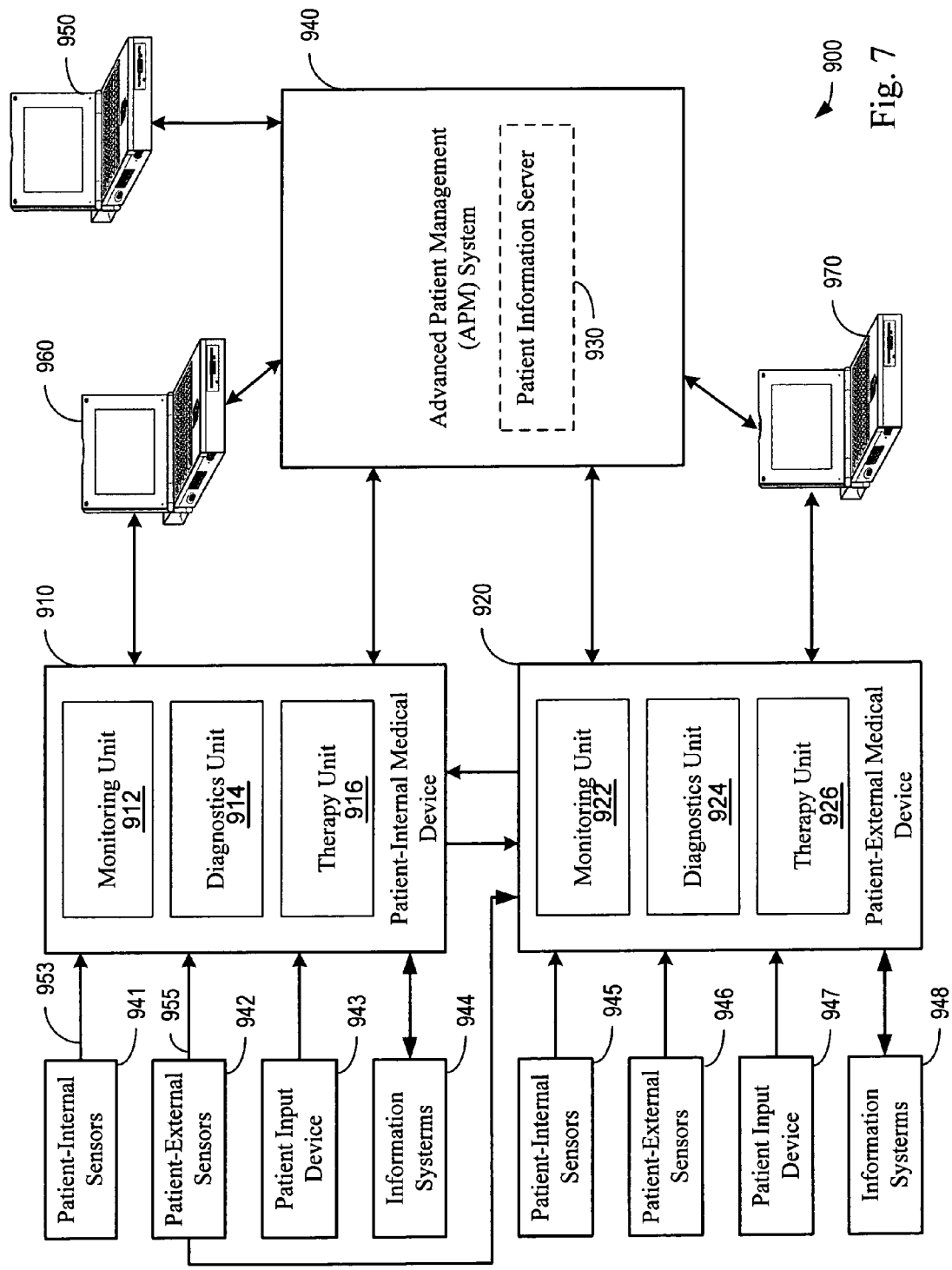
FIG. 7 is a block diagram of a medical system that may be used to implement coordinated patient monitoring, diagnosis, and/or therapy in accordance with embodiments of the invention.

FIG. 7 is a block diagram of a medical system 900 that may be used to implement coordinated patient measuring and/or monitoring, diagnosis, and/or therapy, including detecting EMGs and determining the presence of sleep-related muscle disorders in accordance with embodiments of the invention. The medical system 900 may include, for example, one or more patient-internal medical devices 910 and one or more patient-external medical devices 920. Each of the patient-internal 910 and patient-external 920 medical devices may include one or more of a patient monitoring unit 912, 922, a diagnostics unit 914, 924, and/or a therapy unit 916, 926.

The patient-internal medical device 910 is typically a fully or partially implantable device that performs measuring, monitoring, diagnosis, and/or therapy functions. The patient-external medical device 920 performs monitoring, diagnosis and/or therapy functions external to the patient (i.e., not invasively implanted within the patient's body). The patient-external medical device 920 may be positioned on the patient, near the patient, or in any location external to the patient. It is understood that a portion of a patient-external medical device 920 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 910, 920 may be coupled to one or more sensors 941, 942, 945, 946, patient input devices 943, 947 and/or other information acquisition devices 944, 948. The sensors 941, 942, 945, 946, patient input devices 943, 947, and/or other information acquisition devices 944, 948 may be employed to detect conditions relevant to the monitoring, diagnostic, and/or therapeutic functions of the patient-internal and patient-external medical devices 910, 920.

One or more of sensors 941, 942, 945, 946 may be configured to detect conditions associated with sleep-related muscle disorders. For example, one or more of sensors 941, 942, 945, 946 may be implemented as an EMG sensor, and one or more of sensors 941, 942, 945, 946 may be implemented as a respiration sensor. The EMG and respiration sensors may be coupled to diagnostics unit 914, 924 for detection of sleep-related muscle disorders.

The medical devices 910, 920 may each be coupled to one or more patient-internal sensors 941, 945 that are fully or partially implantable within the patient. The medical devices 910, 920 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 941 may be coupled to the patient-internal medical device 910 through one or more internal leads 953. In one example, as was described above with reference to FIG. 4, an internal endocardial lead system is used to couple cardiac electrodes to an implantable pacemaker or other cardiac rhythm management device. Still referring to FIG. 7, one or more patient-internal sensors 941 may be equipped with transceiver circuitry to support wireless communications between the one or more patient-internal sensors 941 and the patient-internal medical device 910 and/or the patient-external medical device 920. The patient-external sensors 942 may be coupled to the patient-internal medical device 910 and/or the patient-external medical device 920 through one or more internal leads 955 or through wireless connections. Patient-external sensors 942 may communicate with the patient-internal medical device 910 wirelessly. Patient-external sensors 946 may be coupled to the patient-external medical device 920 through one or more internal leads or through a wireless link.

The medical devices 910, 920 may be coupled to one or more patient input devices 943, 947. The patient input devices are used to allow the patient to manually transfer information to the medical devices 910, 920. The patient input devices 943, 947 may be particularly useful for inputting information concerning patient perceptions, such as how well the patient feels, and information such as patient smoking, drug use, or other activities that are not automatically sensed or detected by the medical devices 910, 920.

The medical devices 910, 920 may be connected to one or more information systems 944, 948, for example, a database that stores information useful in connection with the monitoring, diagnostic, or therapy functions of the medical devices 910, 920. For example, one or more of the medical devices 910, 920 may be coupled through a network to a patient information server 930 that provides information about environmental conditions affecting the patient, e.g., the pollution index for the patient's location.

In one embodiment, the patient-internal medical device 910 and the patient-external medical device 920 may communicate through a wireless link between the medical devices 910, 920. For example, the patient-internal and patient-external devices 910, 920 may be coupled through a short-range radio link, such as Bluetooth, IEEE 802.11, and/or a proprietary wireless protocol. The communications link may facilitate unidirectional or bidirectional communication between the patient-internal 910 and patient-external 920 medical devices. Data and/or control signals may be transmitted between the patient-internal 910 and patient-external 920 medical devices to coordinate the functions of the medical devices 910, 920.

In another embodiment, the patient-internal and patient-external medical devices 910, 920 may be used within the structure of an advanced patient management system 940. Advanced patient management systems 940 involve a system of medical devices that are accessible through various communications technologies. For example, patient data may be downloaded from one or more of the medical devices periodically or on command, and stored at the patient information server 930. The physician and/or the patient may communicate with the medical devices and the patient information server 930, for example, to acquire patient data or to initiate, terminate or modify therapy.

The data stored on the patient information server 930 may be accessible by the patient and the patient's physician through one or more terminals 950, e.g., remote computers located in the patient's home or the physician's office. The patient information server 930 may be used to communicate to one or more of the patient-internal and patient-external medical devices 910, 920 to provide remote control of the monitoring, diagnosis, and/or therapy functions of the medical devices 910, 920.

In one embodiment, the patient's physician may access patient data transmitted from the medical devices 910, 920 to the patient information server 930. After evaluation of the patient data, the patient's physician may communicate with one or more of the patient-internal or patient-external devices 910, 920 through the APM system 940 to initiate, terminate, or modify the monitoring, diagnostic, and/or therapy functions of the patient-internal and/or patient-external medical systems 910, 920. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 910, 920 may not communicate directly, but may communicate indirectly through the APM system 940. In this embodiment, the APM system 940 may operate as an intermediary between two or more of the medical devices 910, 920. For example, data and/or control information may be transferred from one of the medical devices 910, 920 to the APM system 940. The APM system 940 may transfer the data and/or control information to another of the medical devices 910, 920.

In one embodiment, the APM system 940 may communicate directly with the patient-internal-and/or patient-external medical devices 910, 920. In another embodiment, the APM system 940 may communicate with the patient-internal and/or patient-external medical devices 910, 920 through medical device programmers 960, 970 respectively associated with each medical device 910, 920.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis and/or therapy functions in accordance with embodiments of the invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of evaluating a pathological condition of a patient, comprising:
   sensing muscle movement signals;
   implantably storing sensed muscle movement data indicative of the sensed muscle movement signals;
   implantably analyzing the stored muscle movement data and detecting a presence of an involuntary muscle movement disorder using the stored muscle movement data;
   detecting whether the patient is asleep;
   providing a first therapy to treat the involuntary muscle movement disorder in response to a determination that the patient is asleep; and
   withholding the first therapy in response to a determination that the patient is not asleep.

2. The method of claim 1, wherein the sensing is performed at least in part internally of the patient.

3. The method of claim 1, wherein detecting the presence of the involuntary muscle movement disorder comprises detecting a sleep-related involuntary muscle movement disorder using the muscle movement signals.

4. The method of claim 1, wherein detecting the presence of the involuntary muscle movement disorder comprises detecting a non-sleep-related involuntary muscle movement disorder using the muscle movement signals.

5. The method of claim 1, wherein detecting the presence of the involuntary muscle movement disorder comprises detecting a disease using the muscle movement signals.

6. The method of claim 1, wherein detecting the presence of the involuntary muscle movement disorder comprises detecting a pathological syndrome using the muscle movement signals.

7. The method of claim 1, wherein the involuntary muscle movement disorder comprises a condition associated with one or more of bruxism, periodic limb movement disorder, restless leg syndrome, muscular dystrophy, muscle inflammation, pinched nerves, peripheral nerve damage, amyotrophic lateral sclerosis, myasthenia gravis, and disc herniation.

8. The method of claim 1, wherein sensing muscle movement signals comprises acquiring at least one of accelerometer data and electromyogram signals.

9. The method of claim 1, wherein information associated with the detected involuntary muscle movement disorder is at least one of, trended, communicated, displayed, or printed.

10. The method of claim 1, further comprising communicating one or both of the sensed muscle movement signals and information associated with the detected involuntary muscle movement disorder to a processing system external of the patient.

11. The method of claim 1, further comprising communicating one or both of the sensed muscle movement signals and information associated with the detected involuntary muscle movement disorder to a processing system internal of the patient.

12. The method of claim 1, wherein sensing the muscle movement signals comprises sensing at least some of the muscle movement signals from one or more intramuscular locations.

13. The method of claim 1, further comprising detecting one or more sleep stages using the muscle movement signals.

14. The method of claim 1, wherein the providing comprises at least one of delivering and controlling the therapy based on one or both of the muscle movement signals and the detected involuntary muscle movement disorder.

15. The method of claim 14, wherein the therapy comprises an internal therapy.

16. The method of claim 1, wherein the providing comprises at least one of delivering and controlling a transcutaneous electric nerve stimulation therapy based on one or both of the muscle movement signals and the detected involuntary muscle movement disorder.

17. A system for evaluating a pathological condition of a patient, comprising:
a sensor configured to sense movement of skeletal musculature;
a first detector coupled to the sensor;
a sleep detector that detects whether the patient is asleep;
implantable memory configured to store sensed data associated with an involuntary muscle movement disorder; and
an implantable processor coupled to the first detector and the sleep detector, the processor configured to analyze the stored data and to determine a presence of the involuntary muscle movement disorder; and
a therapy delivery system coupled to the processor and configured to;
provide a first therapy to treat the involuntary muscle movement disorder in response to a determination that the patient is asleep; and
withhold the first therapy in response to a determination that the patient is not asleep.

18. The system of claim 17, wherein one of the sensor and first detector comprises an implantable component.

19. The system of claim 17, wherein each of the sensor and first detector comprises an implantable component.

20. The system of claim 17, wherein the sensor comprises one or both of an electromyogram (EMG) sensor and an accelerometer.

21. The system of claim 17, wherein the processor is configured to determine presence of a condition associated with one or more of bruxism, periodic limb movement disorder, restless leg syndrome, muscular dystrophy, muscle inflammation, pinched nerves, peripheral nerve damage, amyotrophic lateral sclerosis, myasthenia gravis, and disc herniation.

22. The system of claim 17, further comprising a communication interface coupled to the processor, the communication interface configured to effect connectivity between the processor and a patient-external processing system or network.

23. The system of claim 17, wherein the therapy delivery system comprises a patient-external component.

24. The system of claim 17, wherein the therapy delivery system comprises an implantable component.

25. The system of claim 17, wherein the therapy delivery system is configured to deliver at least one of a drug therapy and a transcutaneous electric nerve stimulation therapy.

26. The system of claim 17, wherein at least one of the sensor and the processor is a component of an implantable cardiac rhythm management device.

27. A system for evaluating a pathological condition of a patient, comprising:
means for sensing muscle movement signals;
means for detecting whether the patient is asleep;
a memory configured to store sensed muscle movement data indicative of the sensed muscle movement signals; and
means for implantably analyzing the stored muscle movement data and for detecting a presence of an involuntary muscle movement disorder using the stored muscle movement data; and
means for providing a first therapy to treat the involuntary muscle movement disorder in response to a determination that the patient is asleep, and for withholding the first therapy in response to a determination that the patient is not asleep.

* * * * *

UNITED STATES PATENT AND TRADEMARK OFFICE
CERTIFICATE OF CORRECTION

PATENT NO. : 7,616,988 B2  Page 1 of 1
APPLICATION NO. : 10/939639
DATED : November 10, 2009
INVENTOR(S) : Jeffrey E. Stahmann et al.

It is certified that error appears in the above-identified patent and that said Letters Patent is hereby corrected as shown below:

On the title page, item [75]: In the Inventors:

"Kent Lee, Fridley, MN (US);" should read --Kent Lee, Shoreview, MN (US);--.

Col. 15, line 29-30: "circuitry 81 0 to" should read --circuitry 810 to--.

In the Claims:

Column 20, Claim 17, line 10: "configured to;" should be --configured to:--.

Signed and Sealed this

Ninth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,616,988 B2 Page 1 of 1
APPLICATION NO. : 10/939639
DATED : November 10, 2009
INVENTOR(S) : Stahmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 763 days.

Signed and Sealed this

Nineteenth Day of October, 2010

David J. Kappos
*Director of the United States Patent and Trademark Office*